(12) United States Patent
Meyer

(10) Patent No.: US 7,925,323 B2
(45) Date of Patent: Apr. 12, 2011

(54) RADIAL ELECTRODE ARRAY

(75) Inventor: Peter F. Meyer, Shrewsbury, MA (US)

(73) Assignee: Tyco Healthcare Group LP, Mansfield, MA (US)

( * ) Notice: Subject to any disclaimer, the term of this patent is extended or adjusted under 35 U.S.C. 154(b) by 0 days.

(21) Appl. No.: 12/571,907

(22) Filed: Oct. 1, 2009

(65) Prior Publication Data

US 2010/0022865 A1 Jan. 28, 2010

Related U.S. Application Data

(62) Division of application No. 11/529,651, filed on Sep. 28, 2006, now Pat. No. 7,616,980.

(60) Provisional application No. 60/798,642, filed on May 8, 2006.

(51) Int. Cl.
*A61B 5/04* (2006.01)

(52) U.S. Cl. ........................................ 600/383; 600/393

(58) Field of Classification Search ................... 600/383, 600/391–393
See application file for complete search history.

(56) References Cited

U.S. PATENT DOCUMENTS

| | | | |
|---|---|---|---|
| 3,752,151 A | 8/1973 | Robichaud |
| 3,805,769 A | 4/1974 | Sessions |
| 3,828,766 A | 8/1974 | Krasnow |
| 3,868,946 A | 3/1975 | Hurley |
| 3,888,240 A | 6/1975 | Reinhold, Jr. et al. |
| 3,901,218 A | 8/1975 | Buchalter |
| 3,998,213 A | 12/1976 | Price |
| 4,027,664 A | 6/1977 | Heavner, Jr. et al. |
| 4,034,854 A | 7/1977 | Bevilacqua |
| 4,077,397 A | 3/1978 | Ellis et al. |
| 4,256,118 A | 3/1981 | Nagel |
| 4,353,372 A | 10/1982 | Ayer |
| 4,365,634 A | 12/1982 | Bare et al. |
| 4,498,480 A | 2/1985 | Mortensen |
| 4,729,377 A | 3/1988 | Granek et al. |
| 4,763,660 A | 8/1988 | Kroll et al. |
| 4,781,200 A | 11/1988 | Baker |
| 4,785,822 A | 11/1988 | Wallace |
| 4,815,964 A | 3/1989 | Cohen et al. |
| 4,895,169 A | 1/1990 | Heath |
| 4,909,260 A | 3/1990 | Salem et al. |
| 4,947,846 A | 8/1990 | Kitagawa et al. |
| 4,957,109 A | 9/1990 | Groeger et al. |
| 5,184,620 A | 2/1993 | Cudahy et al. |

(Continued)

FOREIGN PATENT DOCUMENTS

DE 102004032410 1/2006

(Continued)

OTHER PUBLICATIONS

International Search Report EP07253850 dated Dec. 21, 2007.

(Continued)

*Primary Examiner* — Lee S Cohen
(74) *Attorney, Agent, or Firm* — Lisa E. Winsor, Esq.

(57) ABSTRACT

A sensor array apparatus for monitoring medical signals includes a first flexible substrate defining a central focal point and a second flexible substrate associated with the central focal point. A plurality of medical electrodes are disposed on the periphery of the first flexible substrate and a reference electrode is disposed on the second flexible substrate. A connector is in electrical communication with the medical electrodes and the reference electrode and adapted to connect to an electronic system. Bio-electric information is monitored between one of the medical electrodes and the reference electrode.

11 Claims, 14 Drawing Sheets

U.S. PATENT DOCUMENTS

| | | |
|---|---|---|
| 5,224,479 A | 7/1993 | Sekine |
| 5,263,481 A | 11/1993 | Axelgaard |
| 5,301,680 A | 4/1994 | Rosenberg |
| 5,341,806 A | 8/1994 | Gadsby et al. |
| 5,353,793 A | 10/1994 | Bornn |
| 5,370,116 A | 12/1994 | Rollman et al. |
| 5,405,269 A | 4/1995 | Stupecky |
| 5,442,940 A | 8/1995 | Secker et al. |
| 5,494,032 A | 2/1996 | Robinson et al. |
| 5,507,290 A | 4/1996 | Kelly et al. |
| 5,511,553 A | 4/1996 | Segalowitz |
| 5,546,950 A | 8/1996 | Schoeckert et al. |
| 5,622,168 A | 4/1997 | Keusch et al. |
| 5,685,303 A | 11/1997 | Rollman et al. |
| 5,704,351 A | 1/1998 | Mortara et al. |
| 5,724,984 A | 3/1998 | Arnold et al. |
| 5,785,664 A | 7/1998 | Rosenberg |
| 5,813,979 A | 9/1998 | Wolfer |
| 5,865,740 A | 2/1999 | Kelly et al. |
| 5,865,741 A | 2/1999 | Kelly et al. |
| 5,913,834 A | 6/1999 | Francais |
| 5,916,159 A | 6/1999 | Kelly et al. |
| 5,935,061 A | 8/1999 | Acker et al. |
| 5,938,597 A | 8/1999 | Stratbucker |
| 6,006,125 A | 12/1999 | Kelly et al. |
| 6,032,064 A | 2/2000 | Devlin et al. |
| 6,055,448 A | 4/2000 | Anderson et al. |
| 6,066,093 A | 5/2000 | Kelly et al. |
| 6,115,623 A | 9/2000 | McFee |
| 6,115,624 A | 9/2000 | Lewis et al. |
| 6,122,536 A | 9/2000 | Sun et al. |
| 6,122,544 A | 9/2000 | Organ |
| 6,157,851 A | 12/2000 | Kelly et al. |
| 6,219,568 B1 | 4/2001 | Kelly et al. |
| 6,219,569 B1 | 4/2001 | Kelly et al. |
| 6,232,366 B1 | 5/2001 | Wang et al. |
| 6,240,323 B1 | 5/2001 | Calenzo, Sr. et al. |
| 6,339,720 B1 | 1/2002 | Anzellini et al. |
| 6,360,119 B1 | 3/2002 | Roberts |
| 6,400,977 B1 | 6/2002 | Kelly et al. |
| 6,453,186 B1 | 9/2002 | Lovejoy et al. |
| 6,456,872 B1 | 9/2002 | Faisandier |
| 6,553,246 B1 | 4/2003 | Wenger |
| 6,564,079 B1 | 5/2003 | Cory et al. |
| 6,611,705 B2 | 8/2003 | Hopman et al. |
| 6,623,312 B2 | 9/2003 | Merry et al. |
| 6,636,754 B1 | 10/2003 | Baura et al. |
| 6,647,286 B1 | 11/2003 | Kato et al. |
| 6,654,626 B2 | 11/2003 | Devlin et al. |
| 6,748,797 B2 | 6/2004 | Breed et al. |
| 6,751,493 B2 | 6/2004 | Wenger |
| 6,768,921 B2 | 7/2004 | Organ et al. |
| 6,816,744 B2 | 11/2004 | Garfield et al. |
| 6,847,836 B1 | 1/2005 | Sujdak |
| 6,970,731 B1 | 11/2005 | Jayaraman et al. |
| 6,973,341 B2 | 12/2005 | Watson |
| 6,973,343 B2 | 12/2005 | Wenger |
| 6,980,852 B2 | 12/2005 | Jersey-Willuhn et al. |
| 7,104,801 B1 | 9/2006 | Brodnick et al. |
| 7,146,210 B2 | 12/2006 | Palti |
| 7,150,655 B2 | 12/2006 | Mastrototaro et al. |
| 7,169,107 B2 | 1/2007 | Jersey-Willuhn et al. |
| 7,184,820 B2 | 2/2007 | Jersey-Willuhn et al. |
| 7,197,357 B2 | 3/2007 | Istvan et al. |
| 7,272,428 B2 | 9/2007 | Hopman et al. |
| 7,319,895 B2 | 1/2008 | Klefstad-Sillonville et al. |
| 7,333,850 B2 | 2/2008 | Marossero et al. |
| 2002/0133069 A1 | 9/2002 | Roberts |
| 2002/0188216 A1 | 12/2002 | Kayyali et al. |
| 2004/0073127 A1 | 4/2004 | Istvan et al. |
| 2004/0127802 A1 | 7/2004 | Istvan et al. |
| 2004/0176674 A1 | 9/2004 | Nazeri |
| 2005/0177052 A1 | 8/2005 | Istvan et al. |
| 2006/0073728 A1 | 4/2006 | Zaiken et al. |
| 2007/0038057 A1 | 2/2007 | Nam et al. |
| 2007/0049919 A1 | 3/2007 | Lee, Jr. et al. |
| 2007/0260133 A1 | 11/2007 | Meyer |
| 2008/0033276 A1 | 2/2008 | Ehr et al. |
| 2008/0281309 A1 | 11/2008 | Dunning et al. |

FOREIGN PATENT DOCUMENTS

| | | |
|---|---|---|
| EP | 0766946 | 4/1997 |
| EP | 1050269 | 11/2000 |
| WO | WO 02/053028 | 7/2002 |
| WO | WO 02/099442 | 12/2002 |
| WO | WO 03/084381 | 10/2003 |
| WO | WO 2004/074854 | 9/2004 |
| WO | WO 2005/110263 | 11/2005 |

OTHER PUBLICATIONS

International Search Report EP07 25 1765 dated Mar. 31, 2008.
International Search Report EP07 25 4691 dated Mar. 25, 2008.
International Search Report EP08 16 4409 dated Jan. 27, 2009.
Andreas Boos et al.: "A New Lightweight Fetal Telemetry System"; Dec. 1995, Hewlett-Packard Journal pp. 82-93.

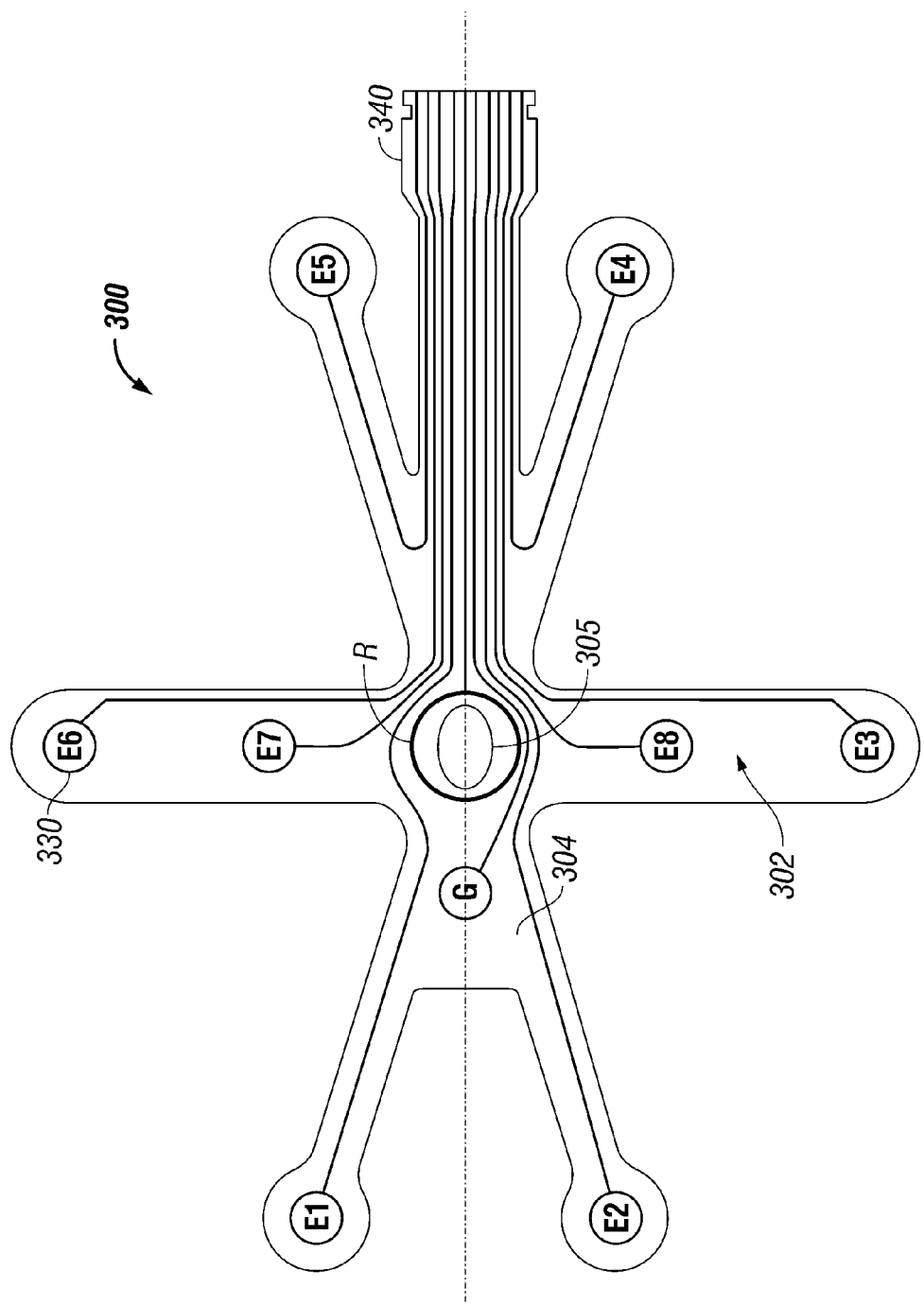

RADIAL ELECTRODE ARRAY

CROSS-REFERENCE TO RELATED APPLICATIONS

This patent application is a divisional application of U.S. patent application Ser. No. 11/529,651, filed Sep. 28, 2006, now U.S. Pat. No. 7,616,980, which claims the benefit of and priority to U.S. Provisional Patent Application No. 60/798,642, filed in the U.S. Patent and Trademark Office on May 8, 2006.

BACKGROUND

1. Technical Field

The present disclosure relates to a sensor array apparatus and, more particularly, relates to a sensor array apparatus for applying an array of electrodes to the body surface of a patient during, for example, maternal and fetal monitoring in connection with intrapartum monitoring and assessment of fetal and maternal well-being.

2. Description of Related Art

Medical electrodes are used to monitor bioelectric signals generated by the body. Electrodes are often covered or coated by a conductive gel, which serves as an electrochemical coupling agent and enhances the ability of the electrode to adhere to a patient's skin. Electrodes are connected to an electronic system, typically a signal monitoring system, and processed for use and analysis by medical personal.

The quality of the information obtained by each electrode is determined by the connection between the electrode and patient skin, the placement of the electrode on the patient relative to the signal source and consistent placement of electrodes relative to each other.

SUMMARY

Accordingly, the present disclosure is directed to an electrode sensor array apparatus useful in a diagnostic application, e.g., maternal and fetal monitoring, to collect clinical data such as maternal electrocardiogram (ECG), maternal uterine electromyogram (EGH), fetal heart rate (FHR), fetal ECG, etc. The sensor array apparatus facilitates accurate and consistent electrode placement on the patient and ensures accurate and consistent placement of electrodes relative to each other during successive uses. The sensor array apparatus is adapted to conform to a non planar surface of the body.

In one embodiment, a sensor array apparatus for monitoring medical signals includes a first flexible substrate defining a central focal point and a second flexible substrate associated with the central focal point. A plurality of medical electrodes are disposed on the periphery of the first flexible substrate and a reference electrode is disposed on the second flexible substrate. A connector is in electrical communication with the medical electrodes and the reference electrode and adapted to connect to an electronic system. Bio-electric information is monitored between one of the medical electrodes and the reference electrode.

The first flexible substrate of the sensor array apparatus may generally define the shape of a circle, triangle, square, rectangle, polygon, or an oval. The electrodes on the first flexible substrate may be disposed at substantially equal predetermined radial distances with respect to the central focal point.

The electrodes may be generally symmetrically arranged on the first flexible substrate about an axis of symmetry whereby a medical electrode on one side of the axis of symmetry has a corresponding medical electrode on the opposite side of the axis of symmetry.

The reference electrode may define at least one reference aperture formed in the second flexible substrate, the reference aperture being dimensioned to partially encapsulate body tissue. The reference electrode may extend around the inner perimeter of the reference aperture and the medical electrodes may each be spaced at substantially equal distances with respect to the reference electrode.

The first flexible substrate and the second flexible substrate may be in mechanical communication and may be in a substantially fixed relationship with respect to each other.

The reference electrode may extend around the inner perimeter of the reference aperture and each of the medical electrodes are a predetermined distance along the skin relative to the reference electrode. The predetermined distance for each electrode may be substantially the same.

In another embodiment, at least one of the plurality of medical electrodes is a monopolar medical electrode in a unipolar arrangement wherein bio-electric information is monitored between the unipolar electrode and the reference electrode.

BRIEF DESCRIPTION OF THE DRAWINGS

Various embodiments of the sensor array apparatus are described herein with reference to the drawings wherein:

FIG. 3 is a view of an alternate embodiment of a sensor array apparatus incorporating a reference electrode surrounding a single reference aperture;

DETAILED DESCRIPTION

Figure 1:
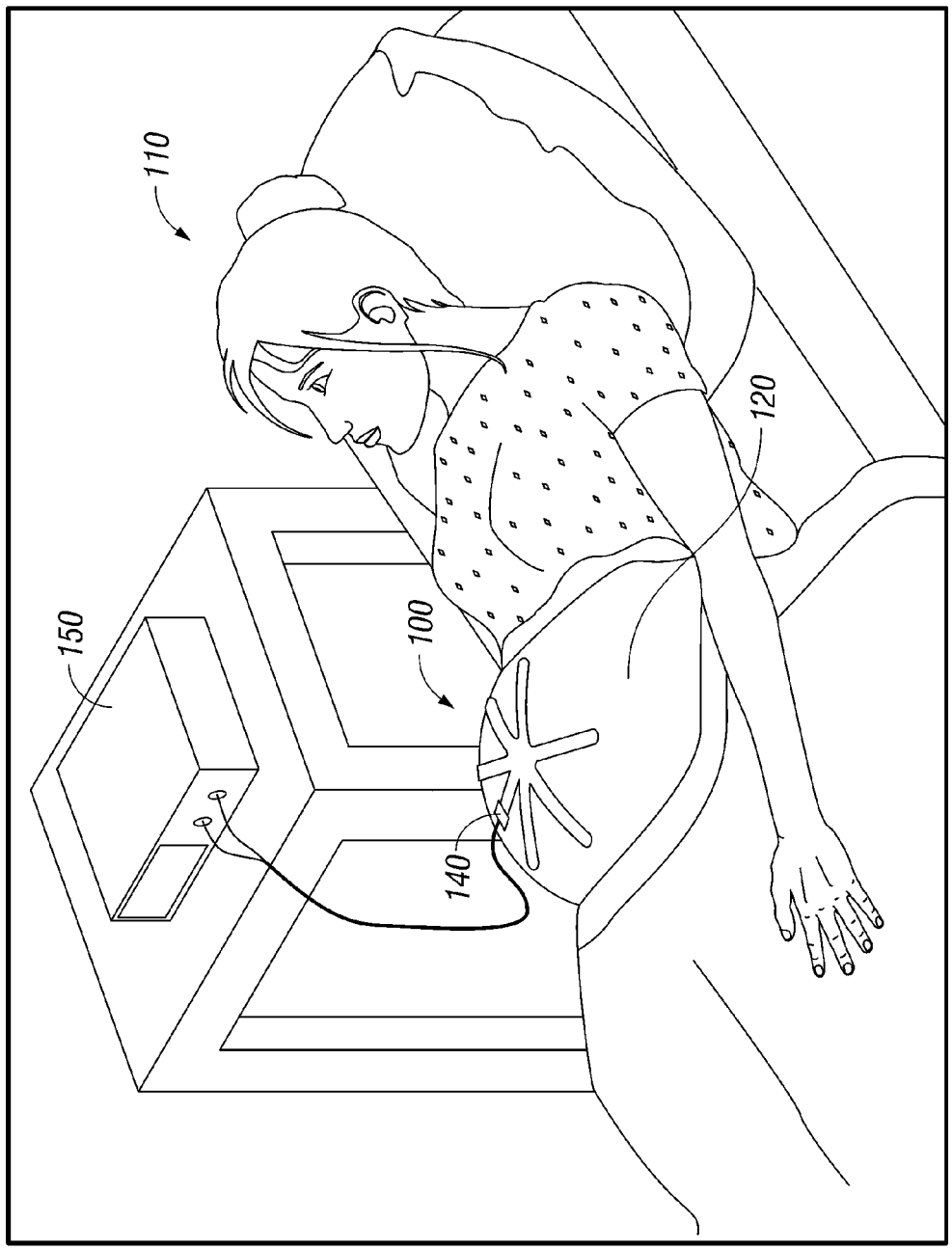
FIG. 1 is a perspective view of a sensor array apparatus for monitoring maternal and fetal bioelectrical signals applied to the abdomen of a full-term pregnant woman.

Embodiments of the presently disclosed sensor array apparatus will now be described in detail with reference to the drawing wherein like reference numerals identify similar or identical elements throughout the several views.

In general, the sensor array apparatus of the present disclosure includes medical electrodes to measure or collect data concerning electrical activity generated within the body. The type of electrode selected, and the placement of the electrode on the body, will determine the type of electrical activity measured. Any type of electrode known in the art may be used with the embodiments of the sensor array apparatuses described herein. The electronic system may be any system known in the art capable of receiving electronic signals. In one preferred embodiment, the sensor array apparatus is a component of an electronic system used in the non-invasive monitoring of maternal-fetal health to extract various parameters including maternal ECG, fetal ECG, maternal and fetal heart rate etc. . . . to ascertain the health and well being of the mother and fetus including such parameters of maternal and fetal distress, progress of labor, estimation of delivery time, etc. Other applications of the sensor array apparatus are also envisioned.

Referring now to FIG. 1, a first embodiment of a sensor array apparatus in accordance with the present disclosure will be discussed. In FIG. 1, sensor array apparatus 100 is illustrated applied to the abdomen 120 of a pregnant female 110 in connection with a maternal and fetal monitoring procedure. Medical electrodes of sensor array apparatus 100 are in contact with the abdomen 120 and in electrical communication with electronic system 150 through connector 140. Electronic system 150 receives bio-electrical medical signals from the sensor array apparatus 100. The bio-electrical medical signals contain information including maternal and fetal ECG and maternal EMG and/or any of the maternal and fetal parameters mentioned hereinabove.

Figure 2A:
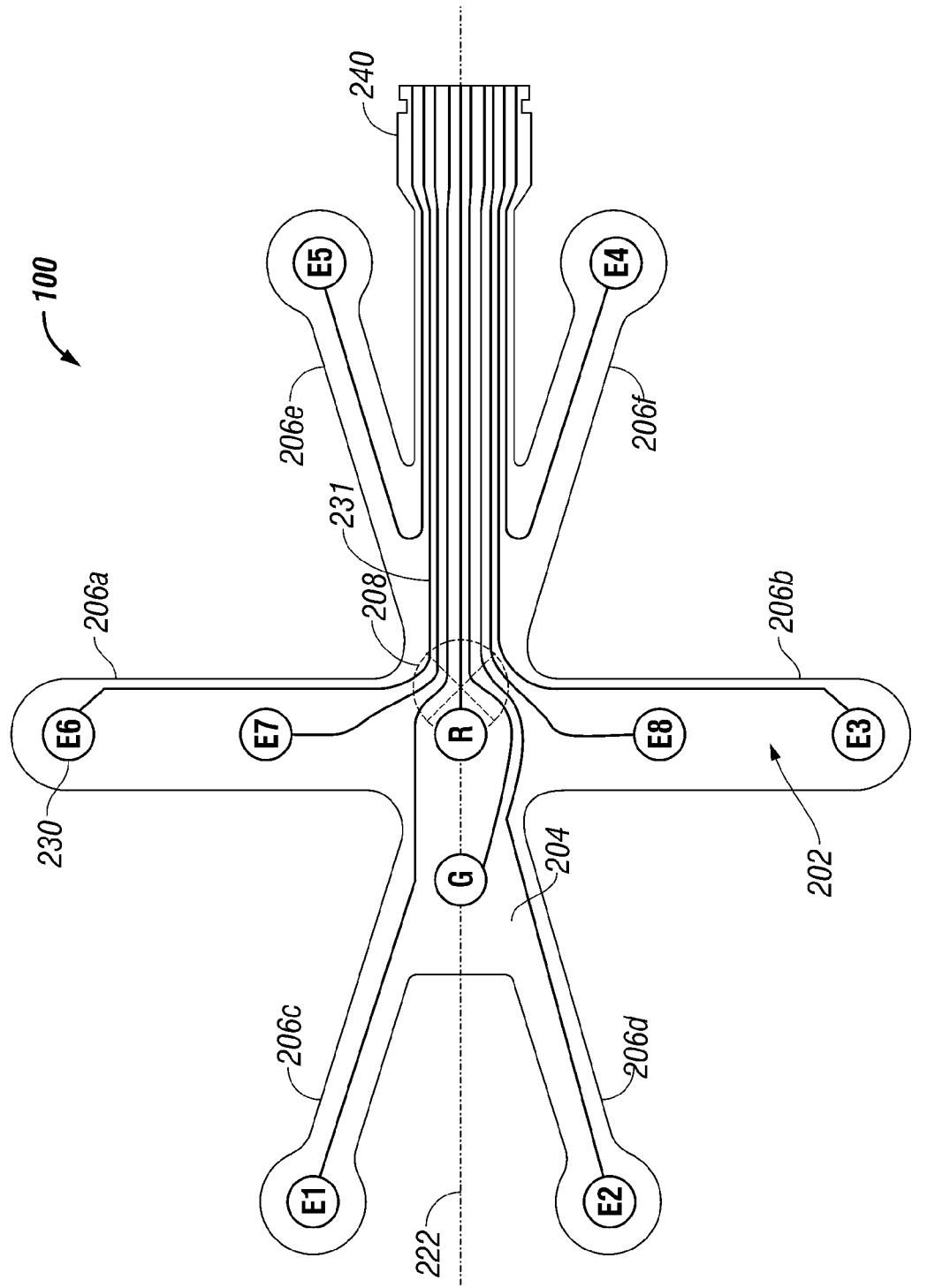
FIG. 2A is a view of the sensor array apparatus of FIG. 1 illustrating the finger-like projections extending radial outwardly from the central portion.

With reference now to FIG. 2A, sensor array apparatus 100 includes flexible substrate 202, medical electrodes E1-E8, reference electrode R, grounded reference electrode G, and connector 240. Flexible substrate 202 is constructed of a flexible material capable of generally conforming to the topography of a skin surface. Preferably, flexible substrate 202 is formed from a material which is sufficiently flexible and sufficiently strong to maintain its position on the patient and the relative positioning of electrodes E1-E8. Suitable materials include Mylar™ or any other biaxially-oriented polyethylene terephthalate polyester films, Teslin™ or any other polyolefin silica blend, natural woven fibers, synthetic non-woven material or paper.

Flexible substrate 202 includes central portion 204 and at least one finger-like projection 206A-206F. Central portion 204 may define central focal point, represented as numeral 208, on the flexible substrate 202. Central focal point 208 corresponds to the central location of substrate 202. Finger-like projections 206A-206F extend radially outwardly from central portion 204. In one preferred embodiment, flexible substrate 202 contains six finger-like projections 206A-206F. However, it is envisioned that flexible substrate 202 may have more or less than six finger-like projections 206.

The specific application determines the shape of the flexible substrate 202 and the number and arrangement of the finger-like projections 206. In FIG. 2A, the flexible substrate 202 and finger-like projections 206A-206F are generally arranged in a symmetrical arrangement with respect to the axis of symmetry 222 which divides the flexible substrate 202 into two sections. Finger-like projections 206A, 206C, 206E are disposed on one side of the axis of symmetry 222 and opposing finger-like projection 206B, 206D, 206F are disposed on the opposite side of the axis of symmetry 222. Thus, sensor apparatus 100 including substrate 202, and, more particularly, the electrode arrangement, is symmetrically arranged about the axis of symmetry 222.

In an alternate embodiment, flexible substrate 202 may be scored or separated along the axis of symmetry 222 into two separate sensor arrays. Such arrangements may facilitate placement of sensor array apparatus on the abdomen. Each half of the sensor array may contain a central portion adjacent a central focal point, finger-like projections extending radially outward from the central portion, medical electrode and a connector adapted to connect to an electronic system.

Returning again to FIG. 2A, each finger-like projections 206A-206F includes at least one electrode E1-E8 in electrical communication with connector 240 which is adapted to connect to an electronic system. Any means for mounting electrodes E1-E8 to substrate 202 are envisioned. One single electrode E1, E2, E5, E4 is disposed on four of the six finger-like projections 206C-206F. Two electrodes E6, E7 and E3, E8 are respectively disposed on finger-like projections 206A, 206B. Electrodes E1-E8 are each a predetermined distance relative to reference electrode R. In FIG. 2A, the respective distances between the reference electrode R and electrodes E1, E2, E4 and E5 are substantially equivalent. Similarly, the respective distances between the reference electrode R and the electrode pair E7, E8 and the electrode pair E3, E6 are substantially equivalent. Thus, when flexible substrate 202 is applied to a non-linear or curved skin surface such as the abdomen of a pregnant female subject, the relative distances of the corresponding electrodes E1-E8 remain proportionally substantially equivalent with respect to reference electrode R and with respect to the remaining corresponding electrodes. Thus, this arrangement provides for accurate and consistent electrode placement on the curved skin surface, which thereby enhances the reliability and accuracy of the clinical data acquired during the monitoring process.

In a preferred system or application, electrodes E1-E8 are unipolar or monopolar electrodes. In a unipolar system, electrodes E1-E8 measure electrical activity relative to reference electrode R. Reference electrode R is generally disposed in central portion 204 of flexible substrate 202 or generally aligned with central focal point 208 of the flexible substrate 202. Electrical activity at each electrode E1-E8 is measured with respect to the reference electrode R. A single reference electrode R is illustrated although it is envisioned that multiple reference electrodes may be utilized.

With continued reference to FIG. 2A, conductive traces 231 place the electrodes E1-E8, R, G and the connector 240 in electrical communication. Conductive traces 231 can be printed directly onto flexible substrate 202 if the flexible substrate 202 is a dielectric. Alternatively, conductive traces 231 may be printed on a separate carrier sheet if flexible substrate 202 is not a dielectric material. Various methods of printing electrical traces 231 include silk screen printing, photoengraving, chemical etching, laser etching or mask electrode. Stretchable conductors, such as stretchable gold strip conductors, may be used with a flexible substrate that exhibits elongation properties as will be discussed.

Flexible substrate 202 may include one or more shielding layers to provide electrical shielding for at least a portion of the conductive traces 231 and/or one or more of the electrodes E1-E8, R.

In use of sensor array apparatus 100 as depicted in FIG. 2A, flexible substrate 202 is applied to, e.g., the abdomen of the female pregnant subject. In one preferred arrangement, the umbilicus is used as a reference point and flexible substrate 202 is positioned onto the abdomen such that central focal point 208 is substantially aligned with the umbilicus. Flexible substrate 202 is arranged about the midline of the patient's abdomen (i.e., the vertical line extending up the abdomen and intersecting the umbilicus) with corresponding finger-like projections 206A-F and electrodes E1-E8 symmetrically arranged about the patient's midline. The electronic system is activated and data is collected by the electrodes E1-E8. This procedure may be repeated several times if desired. With each application, the umbilicus may be used as a reference point for application of flexible substrate 202 thereby ensuring accurate and consistent placement of the electrodes for successive data acquisition procedures.

In an alternative embodiment, flexible substrate 202 of sensor array apparatus 100 may exhibit properties of elongation. With this arrangement, placement on the abdomen may be accomplished by utilizing an electrode placement template. The electrode placement template details the desired arrangement of the electrode array. Thus, when placed on the abdomen, electrode placement locations may be marked on the patient's skin with the use of the template. Each marked location is a predetermined distance along the skin relative to the reference electrode. The marked locations for each unipolar electrode are a predetermined distance from the marked location for the reference electrode. The flexible substrate is elongated and placed on the abdomen such that each electrode is positioned on the marked locations. Multiple templates may ensure proper placement on various sized patients.

With a flexible substrate 202 incorporating elongation characteristics, means may be provided for preventing conductive traces 231 from breaking when flexible substrate 202 is elongated. Such means may include incorporating a zigzag pattern (e.g., accordion-structure or bellows) within conductive traces 231, which straightens when flexible substrate 202 is elongated. Alternatively, portions of flexible substrate 202 and corresponding traces 231 may be folded over such that the folded section provides additional length when the substrate is elongated. As a further alternative, conductive traces 231 may be formed of a material such as gold which exhibits a limited range of stretching or elongation.

Flexible substrate 202 also may be formed of material with an elastic memory. With an elastic memory material, flexible substrate 202 will remain under tension when elongated, but, is biased to return to its original shape. Placing flexible substrate 202 under constant tension would enable the measurement of tension changes due to physical movements of the abdomen by the placement of a strain gauge device on the flexible substrate 202. Flexible substrate 202 may also be formed with materials without elastic memory. Materials without elastic memory exhibit elongation properties but once elongated, remain elongated and do not attempt to return to the original shape and length.

Furthermore, flexible substrate 202 may also be formed with multiple materials with or without elongation properties. Creation of elongation zones would enable some portions of the substrate to stretch, such as the finger-like projections, while sections without elongation properties would maintain in a fixed relationship to each other.

Figure 2B:
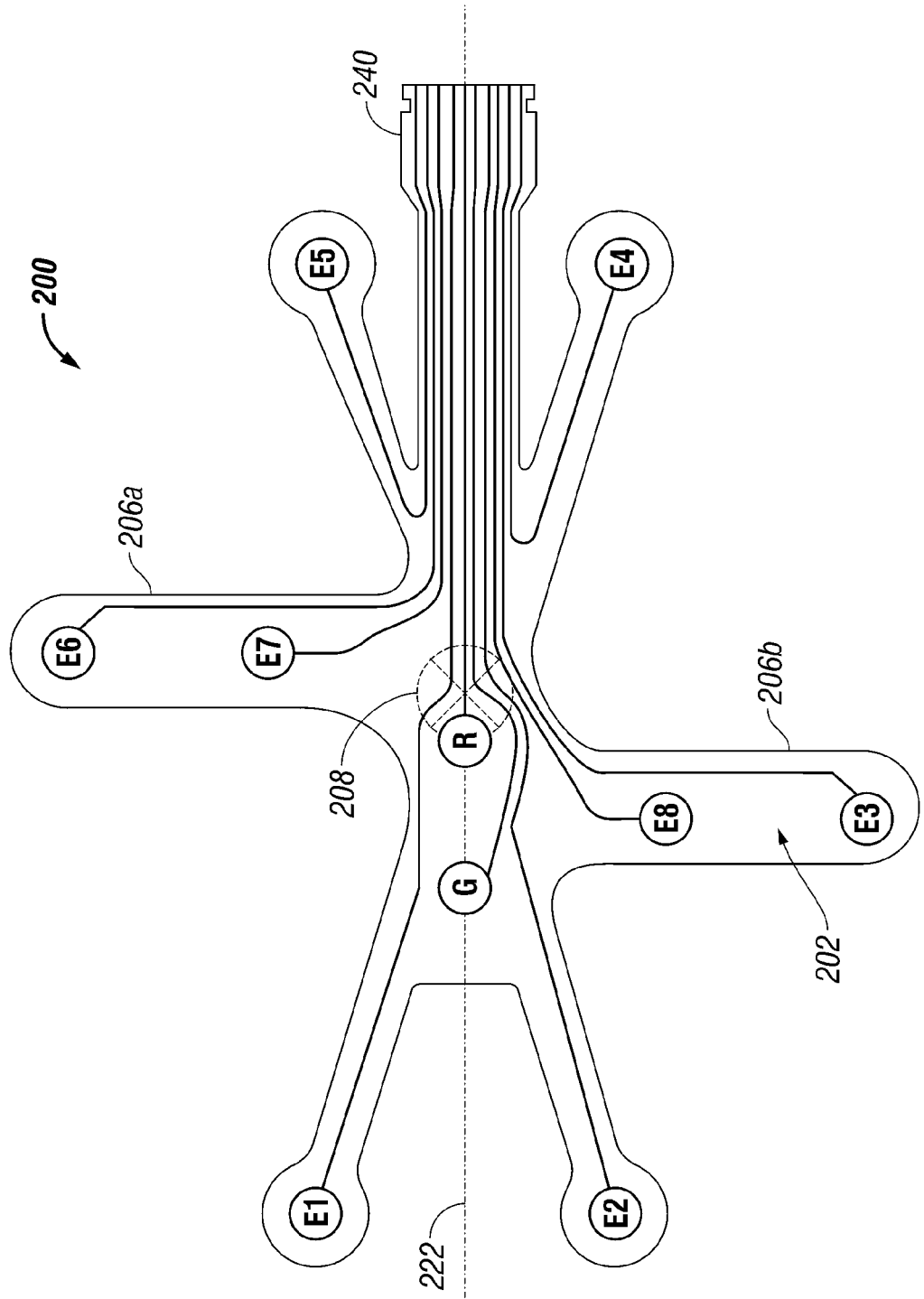
FIG. 2B is a view of an alternative embodiment of a sensor array with asymmetrically arranged finger-like projections.

Referring now to FIG. 2B, finger-like projections 206 of the sensor array apparatus 200 need not be symmetrically arranged. Offset finger-like projections 206a, 206b are not symmetric about the axis of symmetry 222. Offset finger-like projections 206a, 206b extend radially outward from the central portion 208. Electrodes E6, E7 and E3, E8, while disposed on the periphery of the flexible substrate 202, are not symmetrically arranged.

Referring now to FIG. 3, another embodiment of sensor array apparatus 300 is disclosed. Sensor array apparatus 300 contains flexible substrate 302 which defines reference aperture 305. Flexible substrate 302 is designed for placement on the abdomen of a pregnant patient and reference aperture 305 is configured to at least partially encapsulate a body structure such as umbilicus tissue. According to the present disclosure, partially encapsulating a body structure is the placement of a material adjacent to a body structure such that at least a portion of the material partially surrounds or partially encircles the body structure.

Placement of substrate 302 on the patient, with the umbilicus centered in the reference aperture 305, ensures proper and ideal placement of the electrodes E1-E8, R, G on the patient. In general, the body structure is inserted through or positioned under reference aperture 305 to allow the flexible substrate 302 to be placed on the patient skin and accommodate the natural topography or curvature of the body. The body structure may serve as a reference for the medical personnel to ensure proper and consistent placement of the sensor array. The location of the aperture 305 ensures that all electrodes are properly placed relative to the body structure. The shape of aperture 305 may be adjusted to accommodate the specific shape of the body structure and may aid medical personnel by indicating the proper orientation.

In the embodiment of FIG. 3, electrodes E1-E8 are also unipolar. The electronic system (not shown) connects to connector 340 and measures the signal at each electrode relative to a reference electrode R. Reference electrode R surrounds or encircles the reference aperture 305 and the portion of the umbilicus contained therewithin. The electronic system measures the average electrical activity generated between each electrode E1-E8 and reference electrode R at a particular moment in time. The sensor array apparatus 300 provides the electronic system with the average electrical activity at a plurality of locations on the abdomen.

Reference aperture 305 and reference electrode R permit sensor apparatus 300 to be oriented such that the connector 340 can be accessed from either side of the patient. Placement of electrodes E6, E7 between the umbilicus and the pubic region will place the connector on one side of the patient while placement of electrodes E8, E3 between the umbilicus and the pubic region will place the connector on the opposite side of the patient. In both orientations, the electrodes placement pattern on the abdomen is substantially identical.

Figure 4A:
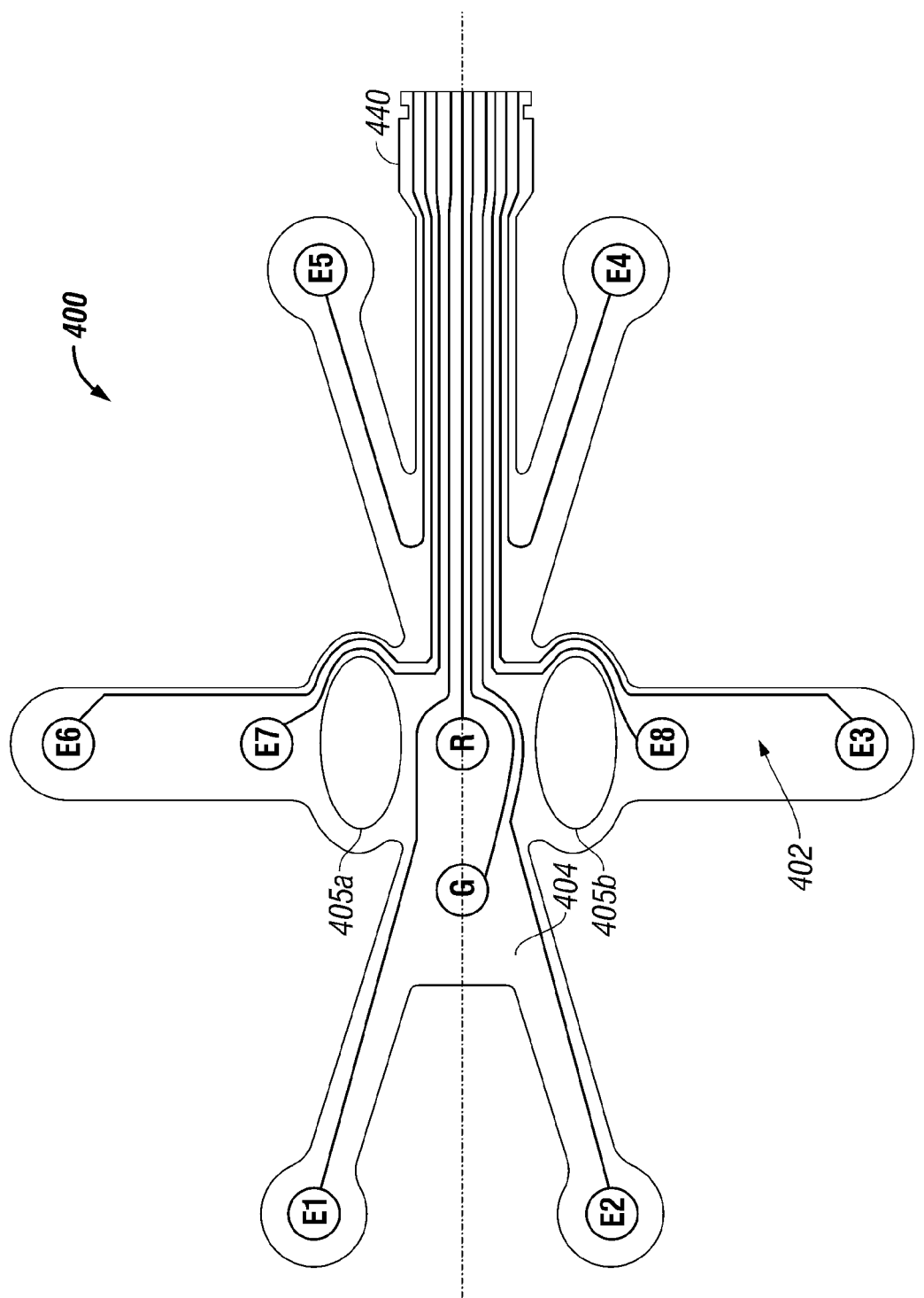
FIGS. 4A and 4B are alternate embodiments of a sensor array apparatus incorporating two reference apertures.

FIG. 4A illustrates another embodiment of sensor array apparatus 400. Flexible substrate 402 defines two reference apertures 405a 405b, each aperture capable of at least partially encapsulating umbilicus tissue. Reference electrode R and grounded reference electrode G are disposed on the central portion between the two reference apertures 405a, 405b. In this embodiment, the proper location of the reference electrode R and the grounded reference electrode G is above the umbilicus. The two reference apertures 405a, 405b on opposing sides of the reference electrode R and grounded reference electrode G allow substantially identical electrode placement patterns on the abdomen, with the reference electrode R and the grounded reference electrode G above the umbilicus, regardless of which side the patient the electrical connector 440 is placed.

Figure 4B:
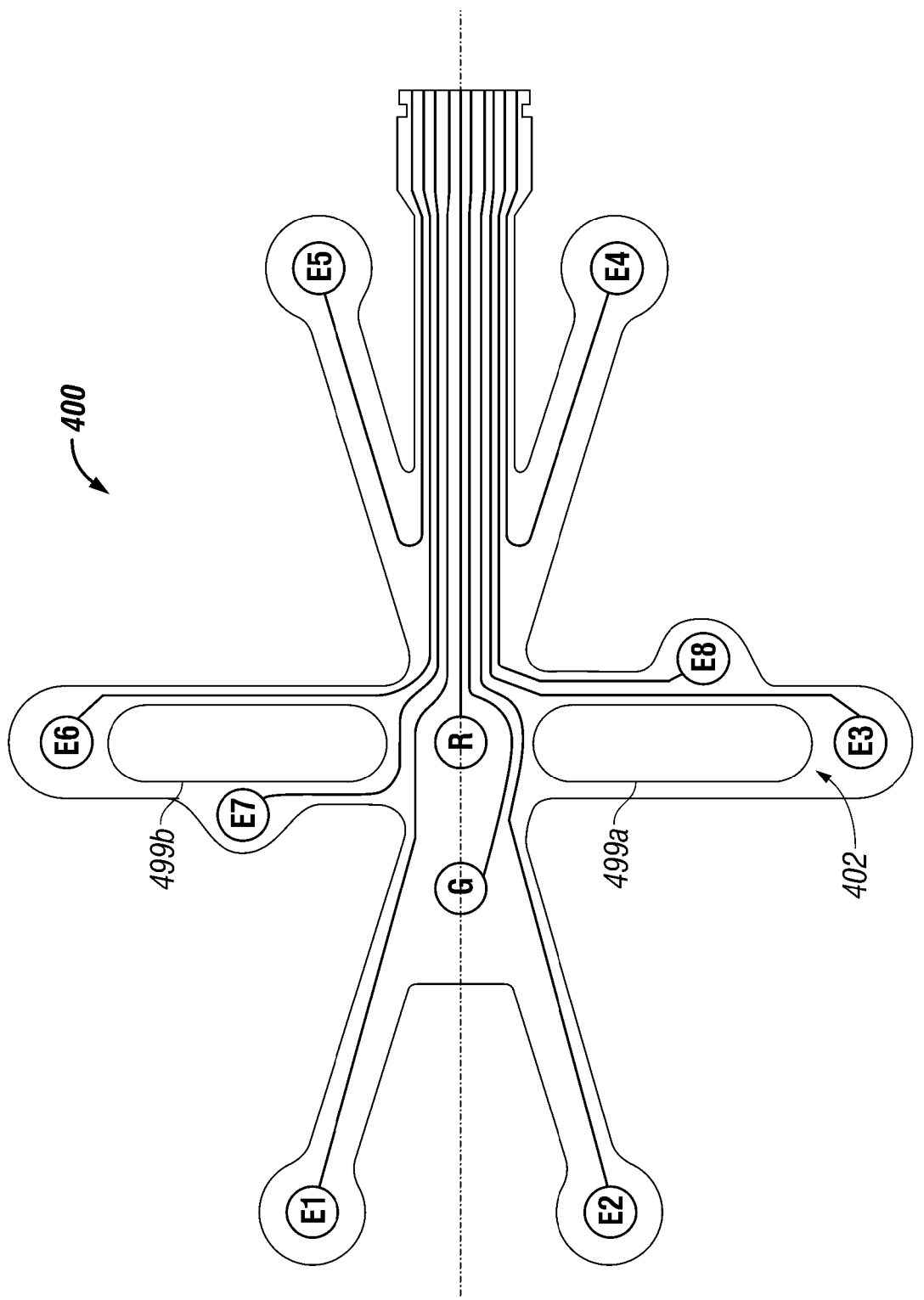

FIG. 4B illustrates finger-like projections 202 with elongated reference apertures 499a, 499b in the sensor array apparatus 400. The body structure may be placed anywhere within the elongated reference apertures 499a, 499b. The elongated reference aperture 499a, 499b permits the placement of the reference electrode R to vary relative to the body structure.

Figure 5A:
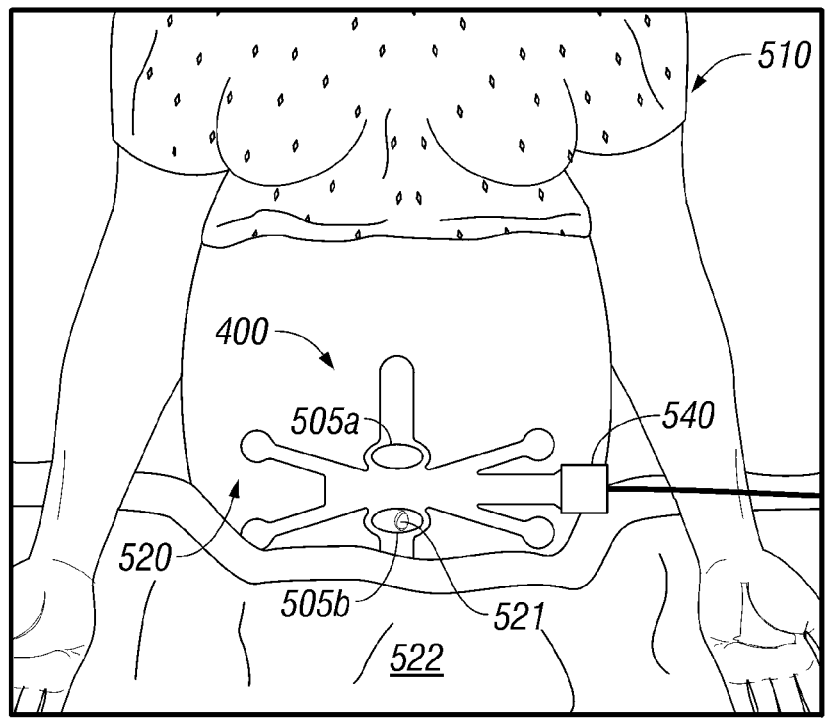
FIGS. 5A and 5B are views of the sensor array apparatus of FIG. 4A applied to the abdomen of a full-term pregnant woman.
Figure 5B:
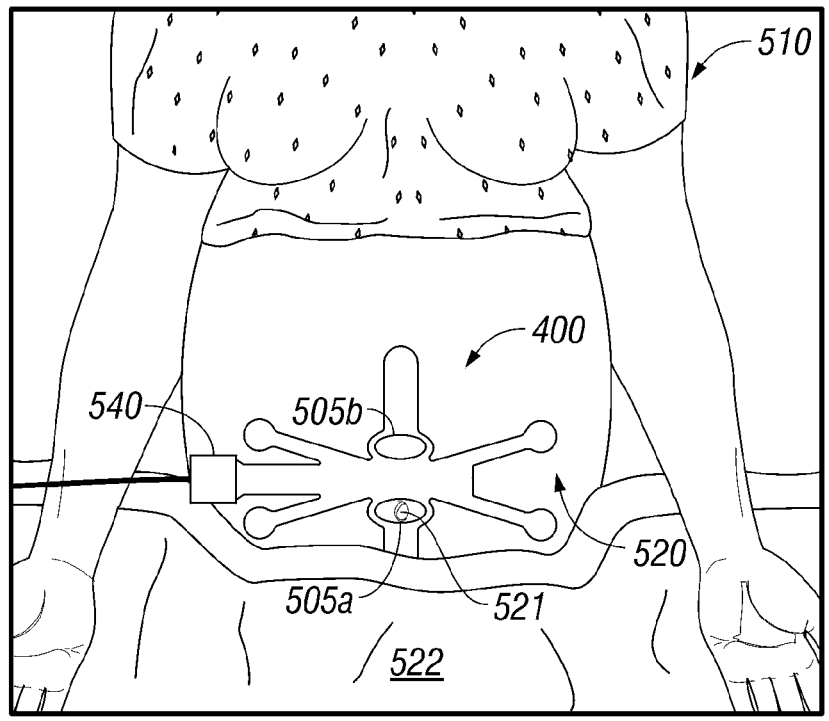

FIGS. 5A and 5B illustrate placement of sensor array apparatus 400 of FIG. 4A on the abdomen 520 of the pregnant patient 510. In FIG. 5A, reference aperture 505b closest to pubis region 522 is positioned such that umbilicus 521, or at least the portion of the umbilicus extending above abdomen 520, protrudes through, or is positioned under, reference aperture 505b. Connector 540 is accessible from the left side of the patient. In FIG. 5B, reference aperture 505a located closest to the pubis region 522 is positioned such that umbilicus 521, or at least the portion of the umbilicus extending above abdomen 520, is protruding through reference aperture 505a. The connector 540 is accessible from the right side of the patient. Reference electrode (not shown) and the grounded reference electrode (not shown), both located between the reference apertures 505a 505b, are properly positioned above the umbilicus in both configurations.

Figure 6A:
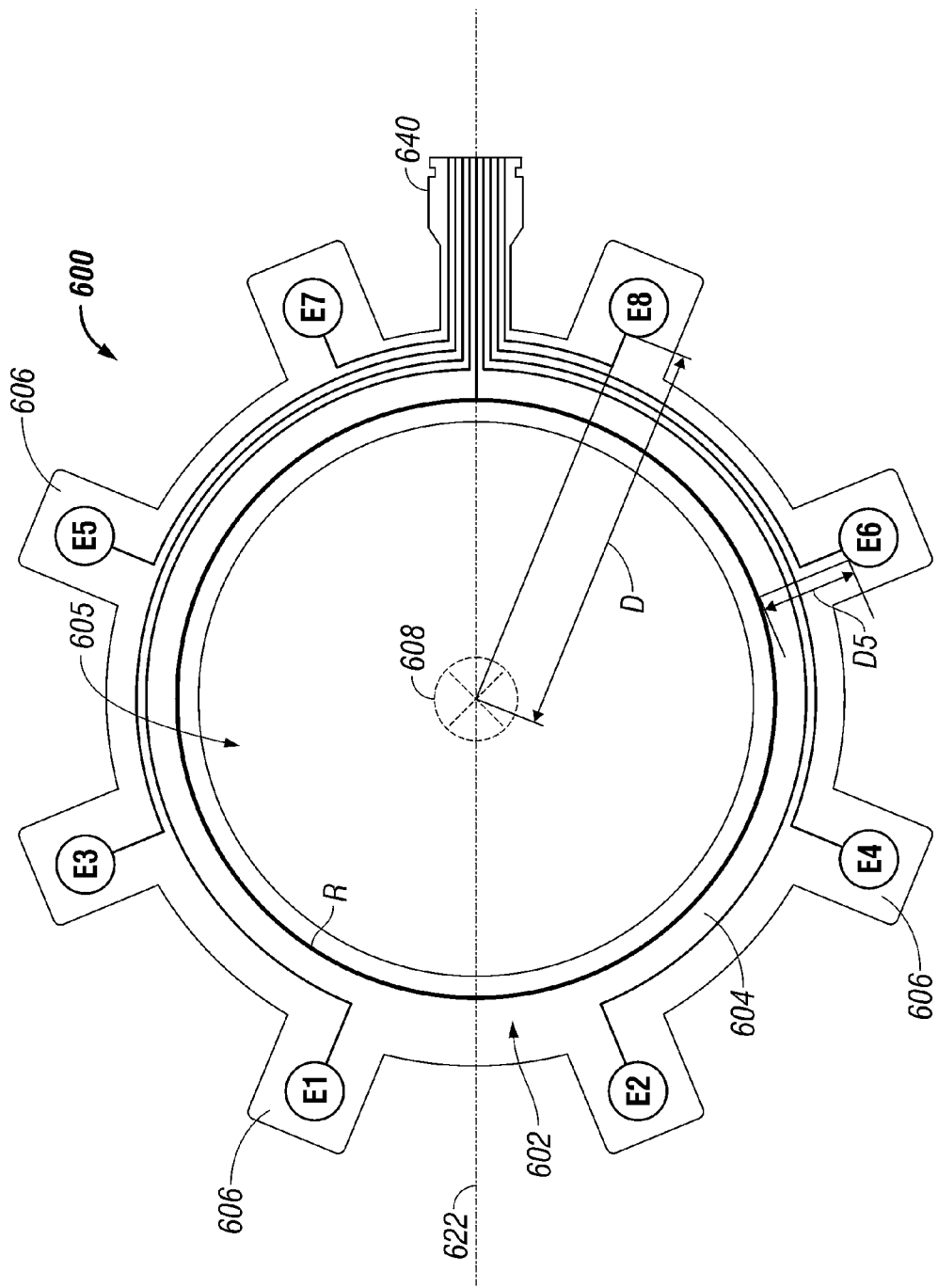
FIG. 6A is a view of another alternate embodiment of the sensor array apparatus incorporating a central focal point.

FIG. 6A illustrates another embodiment of the present disclosure. Sensor array apparatus 600 includes flexible substrate 602 including annular member 604 and a plurality of radial tabs 606 extending radially outwardly from the annular member 604. Annular member 604 defines enlarged central aperture 605 arranged about central focal point 608 which is the proximate center of the flexible substrate 602. A plurality of medical electrodes E1-E8, R is peripherally disposed with respect to the annular member 604. Eight electrodes E1-E8 are disposed on radial tabs 606 adjacent the outer periphery of annular member 604 and an annular reference electrode R is disposed adjacent the inner periphery of the annular member 604. Reference electrode R encircles aperture 605 thereby placing each of the electrodes E1-E8 disposed on radial tabs 606 at substantially equal distances with respect to reference electrode R.

Figure 6B:
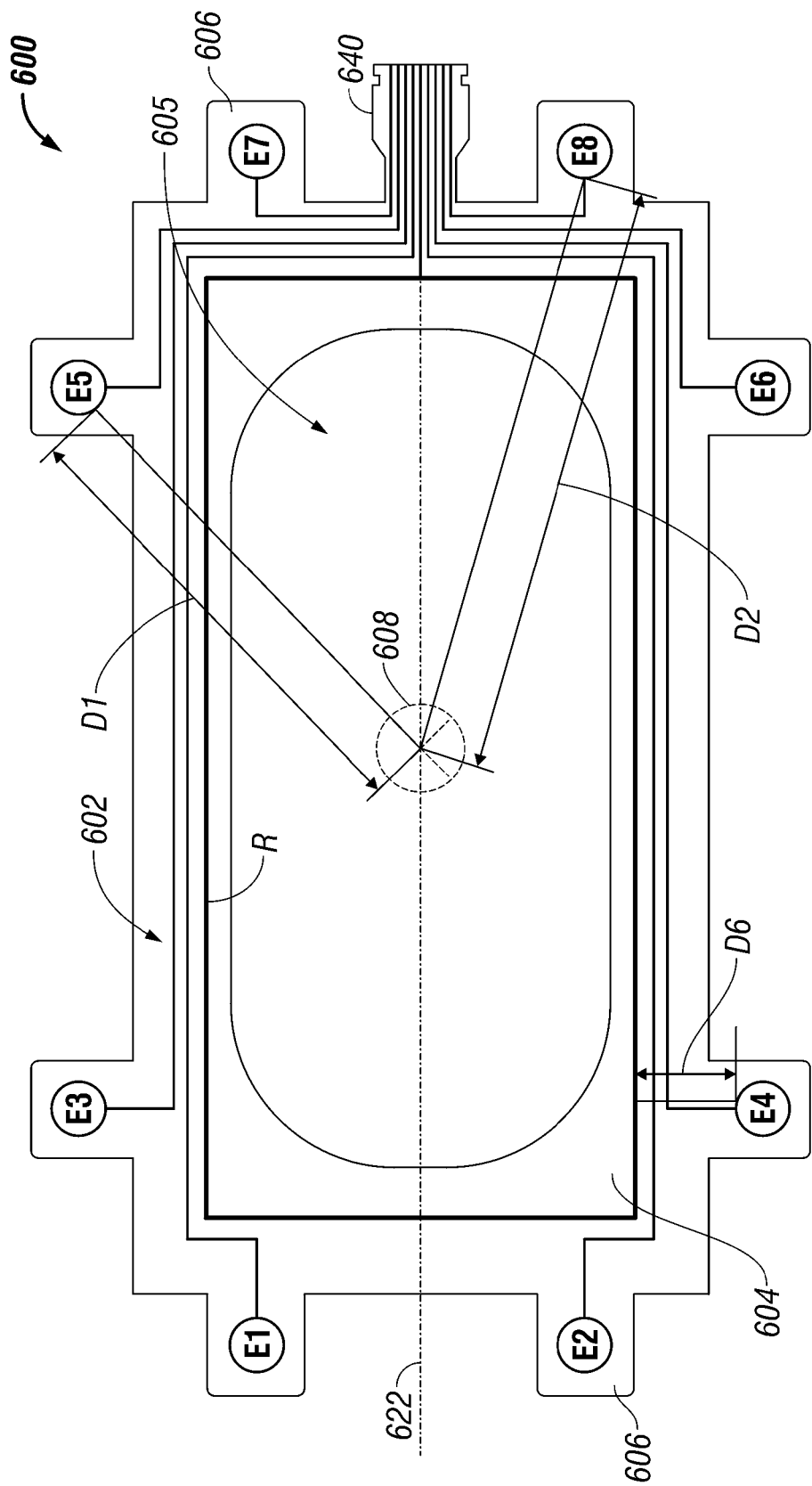
FIGS. 6B, 6C and 6D are views of alternate embodiments of the sensor array apparatus of FIG. 6A.
Figure 6C:
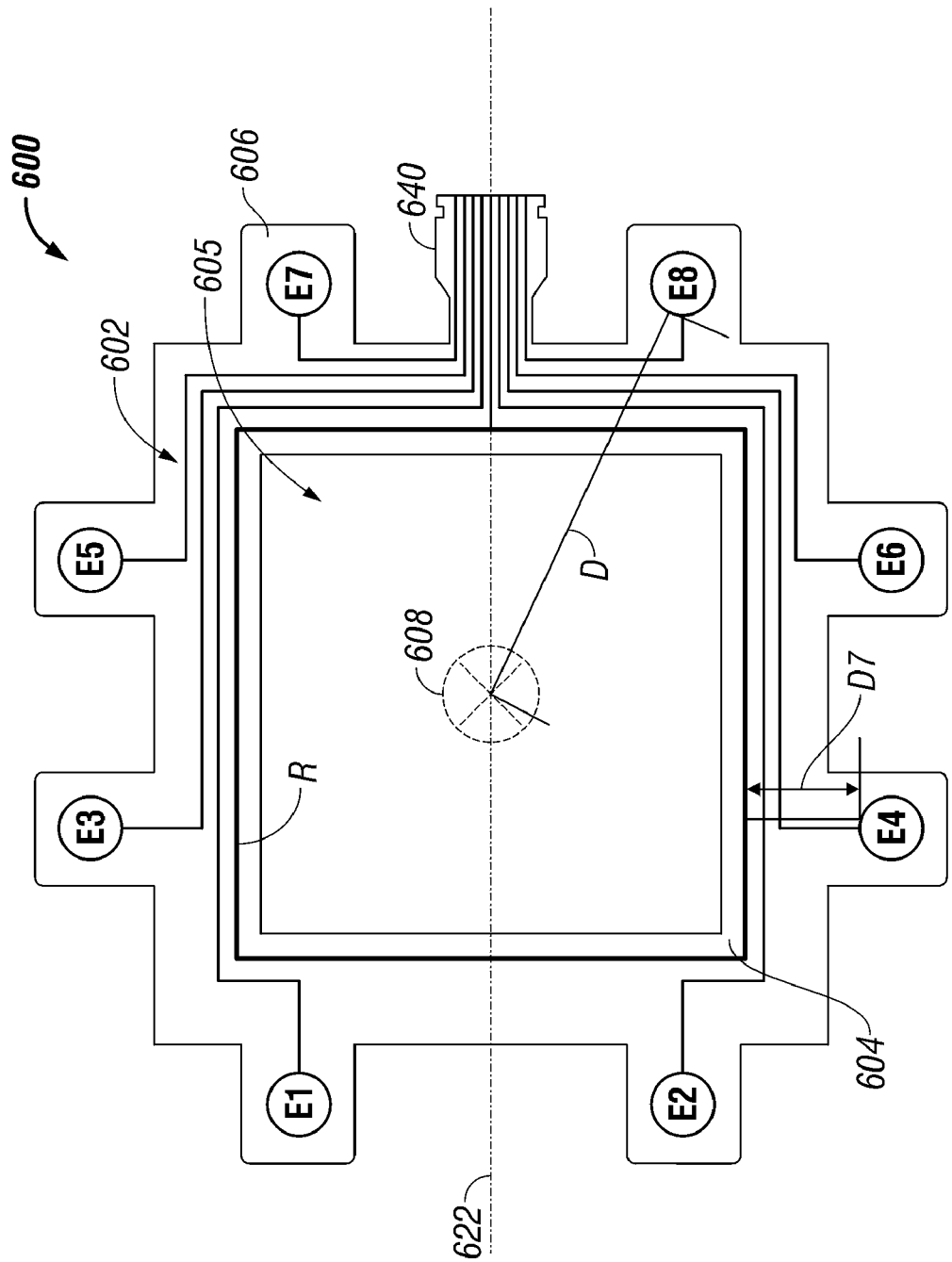
Figure 6D:
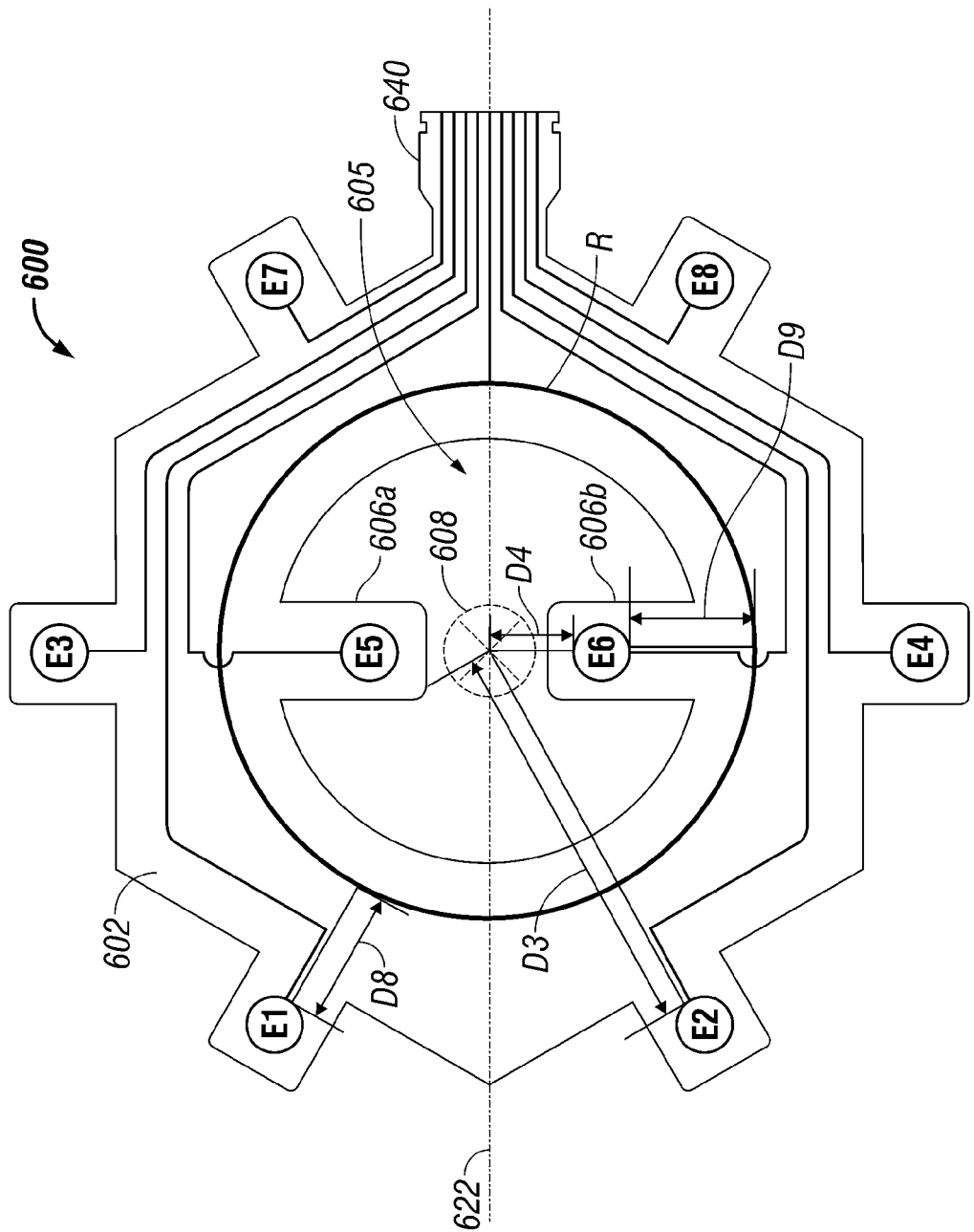

Referring now to FIGS. 6B, 6C and 6D, flexible substrate 602 may be various shapes and sizes. In FIG. 6B, flexible substrate 602 in is generally rectangular shaped with outwardly depending tabs 606. Electrical connector 640 may be disposed on the short side of the rectangle. Eight electrodes E1-E8 are disposed on radial tabs 606 of the flexible substrate 602. A reference electrode R, deposed on the inner periphery of enclosed member 604 of flexible substrate 602, extends around the perimeter of the aperture 605.

Flexible substrate 602 in FIG. 6C is generally square with the electrical connector 640 disposed on a side. Eight electrodes E1-E8 are disposed on radial tabs 606 and reference electrode R, is disposed adjacent the inner periphery of enclosed member 604 of flexible substrate 602 encircling aperture 605.

The flexible substrate 602 in FIG. 6D is generally hexagonal in shape with the electrical connector 640 located at one vertex. Six electrodes E1-E4, E7-E8 are disposed on tabs 606 of flexible substrate 602. Reference electrode R, disposed on the inner periphery of flexible substrate 602, extends around the perimeter of the aperture 605. Two electrodes E5-E6 are disposed on the inner periphery of the apparatus on inwardly finger-like projections 606a, 606b of the flexible substrate 602.

In FIGS. 6A, 6B, 6C, and 6D, the general shape of the flexible substrate 602 define a central focal point 608, with the central focal point 608 adjacent the geometrical center of each shape. Proper positioning of the sensor array apparatus 600 on the abdomen of a pregnant female places the umbilicus adjacent the central focal point 608. In use, the electrodes E1-E8 disposed on tabs 606 of flexible substrate 602 are distributed on the abdomen in predetermined positions relative to each other and the reference electrode R. The average electrical activity between the reference electrode R and each unipolar medical electrode E1-E8 is measured by the electronic system.

Flexible substrate 602 may define one or more apertures with the shape of the apertures being independent of the overall shape of the flexible substrate 602. The apertures in FIGS. 6A, 6B and 6C may be circular, rectangular with rounded corners and square. In FIG. 6D, the shape of the aperture 606 is defined by tabs 606a, 606b which extend into the aperture 607 and positions the electrodes E5, E6 on the inner periphery of flexible substrate 602.

Referring now again to FIG. 6A, the minimum size of the aperture 605 is determined by the curvature of the skin surface and the body structure the aperture 605 must accommodate. The abdomen of a first-trimester pregnant female is relatively flat compared to the abdomen of a full term pregnant female and may require no aperture or a small aperture for the umbilicus. On the other hand, the abdomen of a full term pregnant female, with an extended umbilicus, may require a large aperture and the flexible substrate may be narrow to accommodate the curvature of the abdomen.

The maximum size of the aperture is determined by the shape of the flexible substrate, the number of electrodes, the number and width of the traces printed on the flexible substrate, the location of the electrodes on the abdomen, and the predetermined distance between the reference electrode R and each of the medical electrodes E1-E8.

With continued reference to FIGS. 6A, 6B, 6C and 6D, electrodes E1-E8 disposed on the flexible substrate 602 are arranged in various configurations. In this particular application, the placement of a sensor array apparatus 600 on the abdomen of a pregnant female, electrodes E1-E8 are generally symmetrically arranged about an axis of symmetry 622 with the reference electrode a fixed distance along the skin from each electrode E1-E8. For other applications, the electrodes may not be symmetrically arranged.

With particular reference to FIGS. 6A and 6B, electrodes E1-E8 are positioned a substantially similar predetermined radial distance D with respect to the central focal point 608.

With particular reference to FIGS. 6B and 6D, electrodes are distributed into two groups with the electrodes in each group at a substantially similar predetermined radial distance with respect to the central focal point 608 although the distance for each electrode group is not the same. In FIG. 6B electrodes E3, E4, E5 and E6 are a fixed distance D1 from the central focal point 608 and electrodes E1, E2, E7 and E8 are a fixed distance D2 from the central focal point 608, wherein D1 does not equal D2. In FIG. 6D, electrodes E1, E2, E3, E4, E7 and E8 are a fixed distance D3 from the central focal point 608 and the second group containing electrodes E5, E6 are a distance D4 from the central focal point 608, wherein D3 does not equal D4.

Referring still to FIGS. 6A, 6B, 6C and 6D, electrodes E1-E8 are unipolar electrodes. The electronic system measures the signal at each unipolar electrode E1-E8 relative to a reference electrode R. In FIGS. 6A, 6B, 6C, and 6D, the reference electrode R surrounds or encircles the aperture 605 and places a portion of the reference electrode R a fixed distance from each of the unipolar electrodes E1-E8. In FIGS. 6A, 6B and 6C, the distance from each electrode E1-E8 and the reference electrode R on each sensor array 600 is substantially the same, with the respective distances equal to D5, D6 and D7. In each sensor array apparatus, the distances D5, D6, D7 between the electrodes E1-E8 and the reference electrode R must be sufficiently large to obtain a signal which represents the average electrical activity generated between each electrode and the reference electrode R at a particular moment in time. The plurality of electrodes disposed on sensor array 600 provides the electronic system with the average electrical activity at a plurality of locations on the abdomen.

Referring now to FIG. 6D, the distance from each electrode E1-E8 and the reference electrode R is not equal. The first group of electrodes E1-E4, E7-E8 is a substantially similar distance D8 from the reference electrode R while the second group of electrodes E5, E6 are located a substantially similar distance D9 from the reference electrode R, wherein the two distances D8, D9 are not equal.

Figure 7:
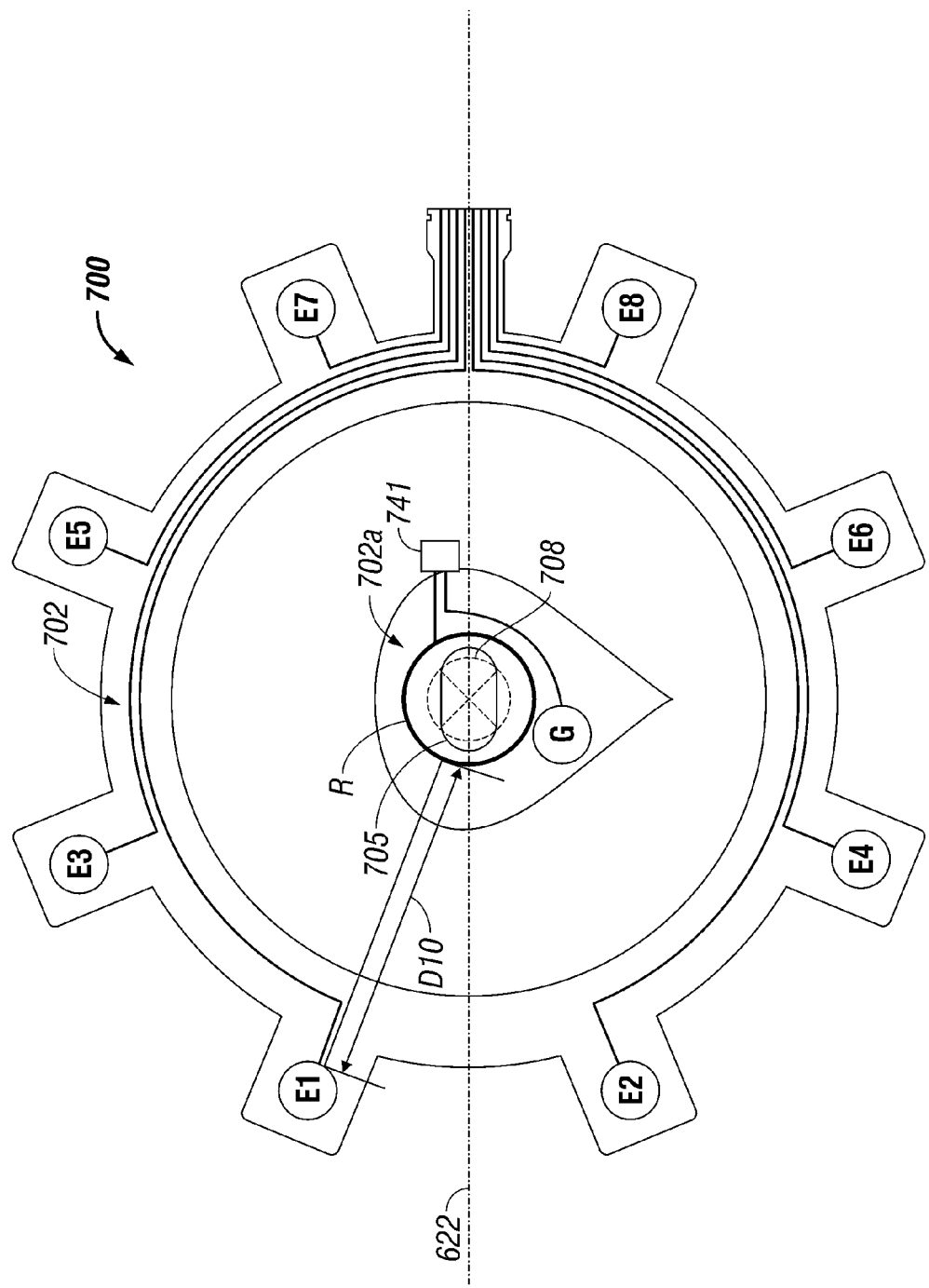
FIG. 7 is a view of another embodiment of the sensor array apparatus incorporating first and second flexible substrate associated with the central focus point.

FIG. 7 illustrates another embodiment of the present disclosure. Sensor array apparatus 700 includes a separate second flexible substrate 702A, associated with the central focal point 708. Reference electrode R and grounded reference electrode G are disposed on second flexible substrate 702A and are in electrical communication with a second connector 741 adapted to connect with an electronic system (not shown). The electronic system (not shown) monitors bio-electrical information between the reference electrode R and each of the medical electrodes E1-E8.

The second flexible substrate 702A defines reference aperture 705 adapted to at least partially encapsulate umbilicus tissue. In FIG. 7, the reference aperture 705 fully encapsulates a portion of the umbilicus. The reference electrode R, disposed on the second flexible substrate 702A extends around the perimeter of the reference aperture 705. A reference electrode R and the grounded reference electrode G are disposed on the second flexible substrate 702A, adjacent the reference aperture 705.

The first and second flexible substrates 702, 702A are both placed on the abdomen relative to the umbilicus. The first flexible substrate 702 is positioned such that central focal point 708 is adjacent the umbilicus and second flexible substrate 702A is positioned such that at least a portion of the umbilicus is positioned within the reference aperture 705. Since the first and second flexible substrates 702,702A are both positioned relative to the umbilicus, the reference electrode R is a predetermined distance from each of the medical electrodes E1-E8. In FIG. 7, the predetermined distance for each electrode D10 is substantially the same. Referring now to FIG. 7, the shape of second flexible substrate 702A assists medical personnel with the proper orientation of the second flexible substrate 702A. In this embodiment, the proper placement of the grounded reference electrode G is below the umbilicus. Pointing the vertex of second flexible substrate 702A toward the pubis region places the grounded reference electrode G in the proper position relative to the umbilicus.

Figure 8:
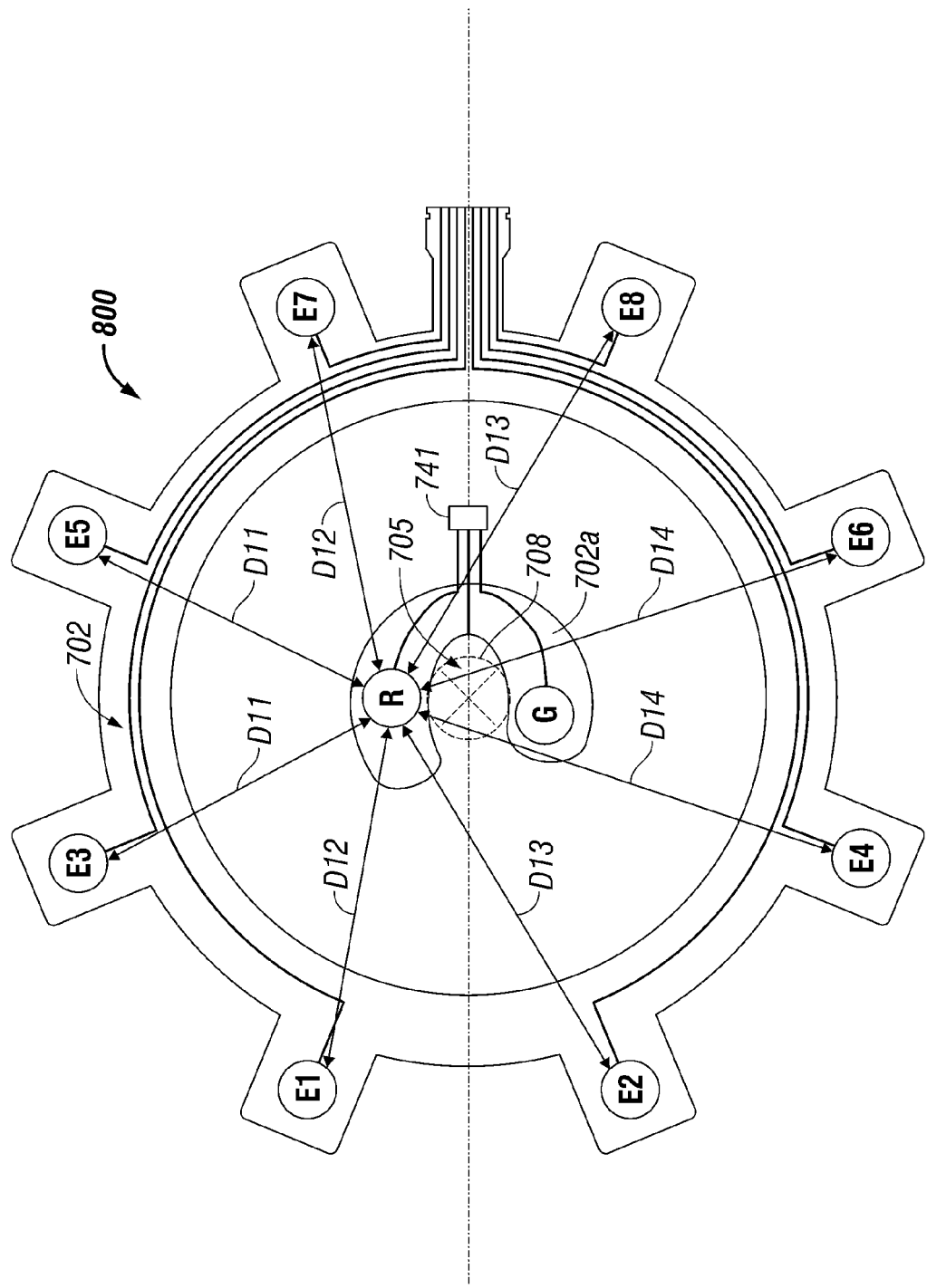
FIG. 8 is a view of another embodiment of sensor array apparatus with a second flexible substrate defining a slot aperture.

FIG. 8 illustrates another alternate embodiment of the present disclosure. In FIG. 8, the distances D11, D12, D13, D14 between the reference electrode R and electrodes in four sets of electrode are substantially the same, while the distance for each set of pairs are not equal (i.e. D11≠D12≠D13≠D14.)

Figure 9:
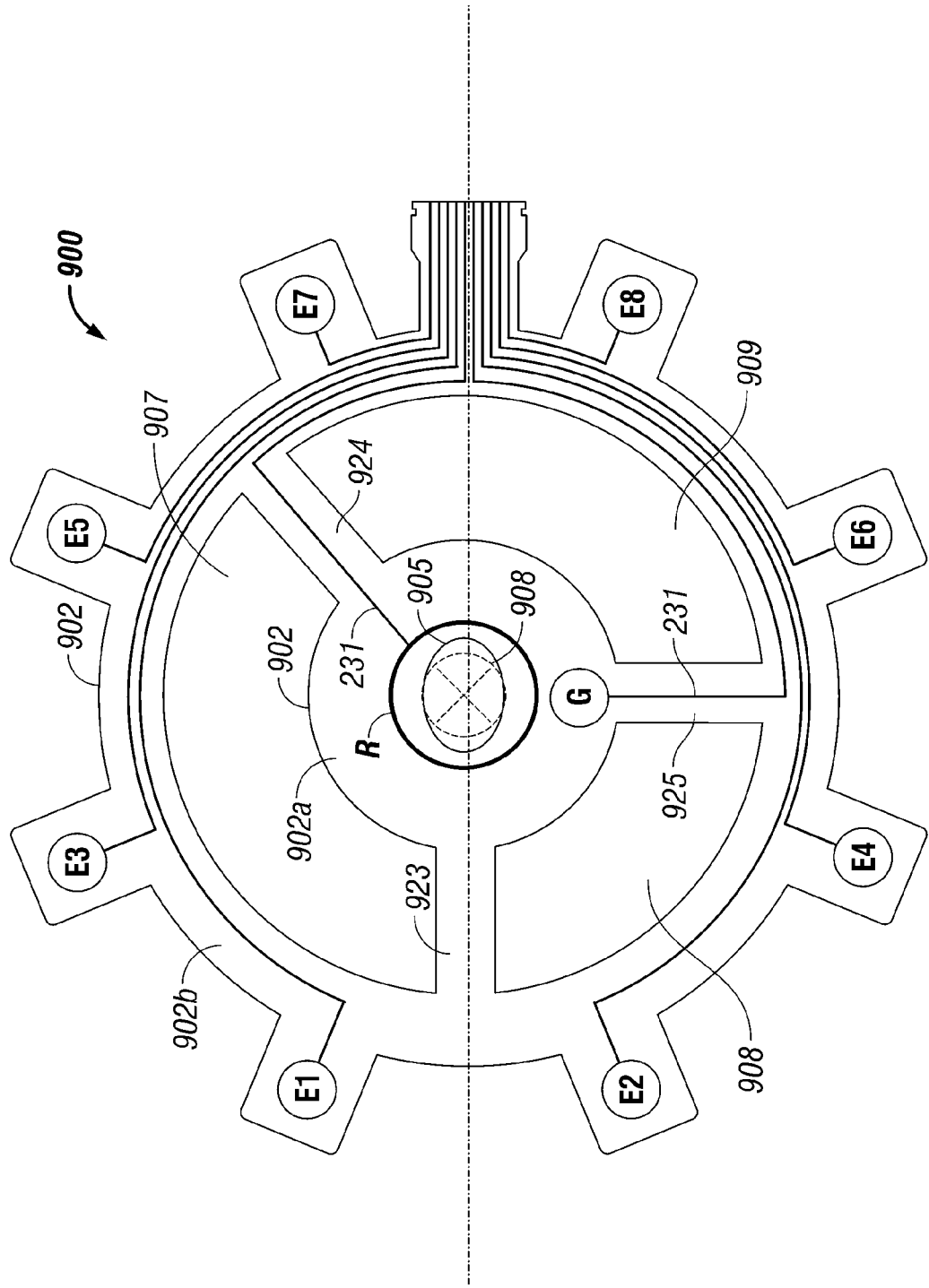
FIG. 9 is a view of another embodiment of sensor array apparatus with a flexible substrate with first and second sections wherein the first section of the flexible substrate is associated with the central portion and the second portion of the flexible substrate is associated with the periphery.

FIG. 9 illustrates another embodiment. Sensor array apparatus 900 includes a flexible substrate 902, a first section 902A associated with the central focal point 908 and defining a first flexible substrate and a second section 902B associated with the outer periphery and defining a second flexible substrate. The first and second sections 902A, 902B are mechanically connected and define at least one aperture between the first and second sections 902A, 902B. In the preferred embodiment, first and second sections 902A, 902B are connected through respective radial links 923, 924, 925 and define three apertures 907, 908, 909.

First section 902A also defines reference aperture 905. As discussed in the prior embodiments, reference aperture 905 at least partially encapsulates a portion of the umbilicus when placed on the abdomen of a pregnant female. In use, the placement of the umbilicus within the reference aperture 905 ensures proper placement of the sensor array 900 on the abdomen.

Reference electrode R and grounded reference electrode G are disposed on the first section 902A of the flexible substrate 902. In this particular embodiment, reference electrode R surrounds reference aperture 905 insuring the distance between the reference electrode R and each of the medical electrodes, E1-E8, is a predetermined distance and the predetermined distance for each electrode E1-E8 is substantially the same. The reference electrode R and the grounded reference electrode G are in electrical communications by traces 231 printed on the flexible substrate 902.

It is to be understood that the foregoing description is merely a disclosure of particular embodiments and is in no way intended to limit the scope of the disclosure. Other possible modifications will be apparent to those skilled in the art and are intended to be within the scope of the present disclosure.

It is still further envisioned for several of the disclosed embodiments to be used in combination with each other.

What is claimed is:

1. A sensor array apparatus for monitoring medical signals, which comprises:
   a first flexible substrate defining a central focal point;
   a plurality of medical electrodes disposed on the periphery of the first flexible substrate;
   a second flexible substrate associated with the central focal point;
   a reference electrode disposed on the second flexible substrate;
   at least one connector in electrical communication with the medical electrodes and the reference electrode, the at least one connector adapted to connect to an electronic system,
   wherein bio-electric information is monitored between at least one of the medical electrodes and the reference electrode.

2. The sensor array apparatus according to claim 1 wherein the first flexible substrate generally define a shape selected from a group consisting of a circle, triangle, square, rectangle, polygon, or oval.

3. The sensor array apparatus according to claim 1 wherein the medical electrodes are disposed at substantially equal predetermined radial distances with respect to the central focal point.

4. The sensor array apparatus according to claim 1 wherein the medical electrodes are generally symmetrically arranged on the first flexible substrate about an axis of symmetry whereby a medical electrode on one side of the axis of symmetry has a corresponding medical electrode on the opposite side of the axis of symmetry.

5. The sensor array apparatus according to claim 1 wherein the reference electrode defines at least one reference aperture formed in the second flexible substrate wherein the at least one reference aperture is dimensioned to partially encapsulate a body tissue.

6. The sensor array apparatus according to claim 5 wherein the reference electrode extends around the inner perimeter of the at least one reference aperture.

7. The sensor array apparatus according to claim 6 wherein the plurality of medical electrodes are each spaced at substantially equal distances with respect to the reference electrode.

8. The sensor array apparatus according to claim 1 wherein the first flexible substrate and the second flexible substrate are in mechanical communication.

9. The sensor array apparatus according to claim 8 wherein the first flexible substrate and the second flexible substrate are in a substantially fixed relationship with respect to each other.

10. The sensor array apparatus according to claim 9 wherein the reference electrode extends around the inner perimeter of the reference aperture and the reference electrode and each of the plurality of medical electrodes are adapted to be along the skin of a patient during use, wherein each of the plurality of medical electrodes are a predetermined distance along the skin relative to the reference electrode, whereby the predetermined distance for each electrode is substantially the same.

11. The sensor array apparatus according to claim 1 wherein at least one of the plurality of medical electrodes further includes:

at least one monopolar medical electrode in a unipolar arrangement wherein bio-electric information is monitored between at least one of the unipolar electrodes and the reference electrode.

* * * * *